(12) United States Patent
Alpenfels et al.

(10) Patent No.: US 7,153,403 B2
(45) Date of Patent: Dec. 26, 2006

(54) PROTEIN MARKET PELLETS AND METHOD OF MAKING AND USING THE SAME

(75) Inventors: William F. Alpenfels, Del Mar, CA (US); Patricia Marilu Vilalta, San Diego, CA (US)

(73) Assignee: PageGel, Inc., San Diego, CA (US)

( * ) Notice: Subject to any disclaimer, the term of this patent is extended or adjusted under 35 U.S.C. 154(b) by 651 days.

(21) Appl. No.: 10/417,055

(22) Filed: Apr. 15, 2003

(65) Prior Publication Data

US 2003/0196897 A1 Oct. 23, 2003

Related U.S. Application Data

(60) Provisional application No. 60/374,109, filed on Apr. 9, 2002.

(51) Int. Cl.
*G01N 27/447* (2006.01)
*G01N 27/453* (2006.01)
*G01N 31/00* (2006.01)

(52) U.S. Cl. .................... 204/456; 204/466; 204/605; 204/616; 252/408.1; 436/15

(58) Field of Classification Search ........ 204/600–618, 204/450–467; 252/408.1; 436/15
See application file for complete search history.

(56) References Cited

U.S. PATENT DOCUMENTS

| | | | | |
|---|---|---|---|---|
| 4,999,340 A | * | 3/1991 | Hoffman et al. | 514/23 |
| 5,102,518 A | * | 4/1992 | Doering et al. | 204/462 |
| 5,705,649 A | * | 1/1998 | Shultz et al. | 548/126 |
| 5,922,186 A | * | 7/1999 | Shukla et al. | 204/606 |

\* cited by examiner

*Primary Examiner*—Alex Noguerola
(74) *Attorney, Agent, or Firm*—Stephen C. Beuerle; Procopio Cory Hargreaves & Savitch LLP

(57) ABSTRACT

A protein marker pellet for use in a gel electrophoresis system includes one or more protein markers including a protein of known molecular weight with ionic components to provide electrical conductance, and a non-protein, gel-forming material having a porosity sufficient to allow the one or more protein markers to migrate out of the protein marker pellet under the influence of an electrical field at the same rate as the ionic components.

38 Claims, 2 Drawing Sheets

PROTEIN MARKET PELLETS AND METHOD OF MAKING AND USING THE SAME

This application claims priority from U.S. provisional application No. 60/374,109, filed Apr. 19, 2002.

FIELD OF THE INVENTION

The invention relates to a protein markers for protein gel electrophoresis.

BACKGROUND OF THE INVENTION

A device used for calibrating protein gel electrophoresis separations is a liquid protein marker. A liquid protein marker includes at least one protein of known molecular weight marked with a tracking dye and ionic components to provide electrical conductance. The protein migrates out of the mixture under the influence of an electrical field at the same rate as the ions. After gel electrophoresis, the migration pattern of a number of protein samples is compared to the migration pattern of the liquid protein marker to determine size or other characteristics of the protein samples.

A problem with liquid protein markers is that they have to be pipetted into wells of the reservoirs. This pipetting step can be burdensome and adds time to the overall process, especially if a large number of gels are loaded (e.g., loading eight gels simultaneously with 96-well automated loaders). Another problem is that with wide wells such as 7.5 mm wide wells, a large volume of the liquid protein marker solution must be added to provide sufficient sensitivity during electrophoresis of the marker. This can significantly increase the cost of a gel run because of the expense of the marker solution. Also, marker solutions must be kept at such low temperatures that they freeze. Repeated freeze/thaw cycles of the marker solution can cause degradation of proteins. A further problem is that only one marker solution can be added per well because multiple marker solutions would mix, giving confusing results.

SUMMARY OF THE INVENTION

Accordingly, an aspect of the invention involves a protein marker pellet for use in a gel electrophoresis system. The protein marker pellet includes one or more protein markers including a protein of known molecular weight with ionic components to provide electrical conductance, and a non-protein, gel-forming material having a porosity sufficient to allow the one or more protein markers to migrate out of the protein marker pellet under the influence of an electrical field at the same rate as the ionic components.

Another aspect of the invention involves a method of making a protein marker pellet for use in a gel electrophoresis system. The method includes providing a protein marker solution including one or more protein markers having a protein of known molecular weight with ionic components to provide electrical conductance; providing a non-protein, gel-forming solution; warming the protein marker solution and the gel-forming solution; combining the protein marker solution and the gel-forming solution to form a protein marker gel solution; providing the protein marker gel solution into multiple small volumes of protein marker gel solution; and allowing the multiple small volumes of protein marker gel solution to set so as to form multiple protein marker pellets having a porosity sufficient to allow the protein marker to migrate out of the protein marker pellet under the influence of an electrical field at the same rate as the ionic components.

A still further aspect of the invention involves a method of using a protein marker pellet with a gel electrophoresis system including multiple wells and an electrophoresis gel. The method includes providing a protein marker pellet including one or more protein markers having a protein of known molecular weight with ionic components to provide electrical conductance, and a non-protein, gel-forming material having a porosity sufficient to allow the protein marker to migrate out of the protein marker pellet under the influence of an electrical field at the same rate as the ionic components; depositing the protein marker pellet in one of the wells of the gel electrophoresis system; and causing the protein marker to migrate out of the protein marker pellet under the influence of an electrical field.

Further objects and advantages will be apparent to those skilled in the art after a review of the drawings and the detailed description of the preferred embodiments set forth below.

DETAILED DESCRIPTION OF PREFERRED EMBODIMENTS

Figure 1:
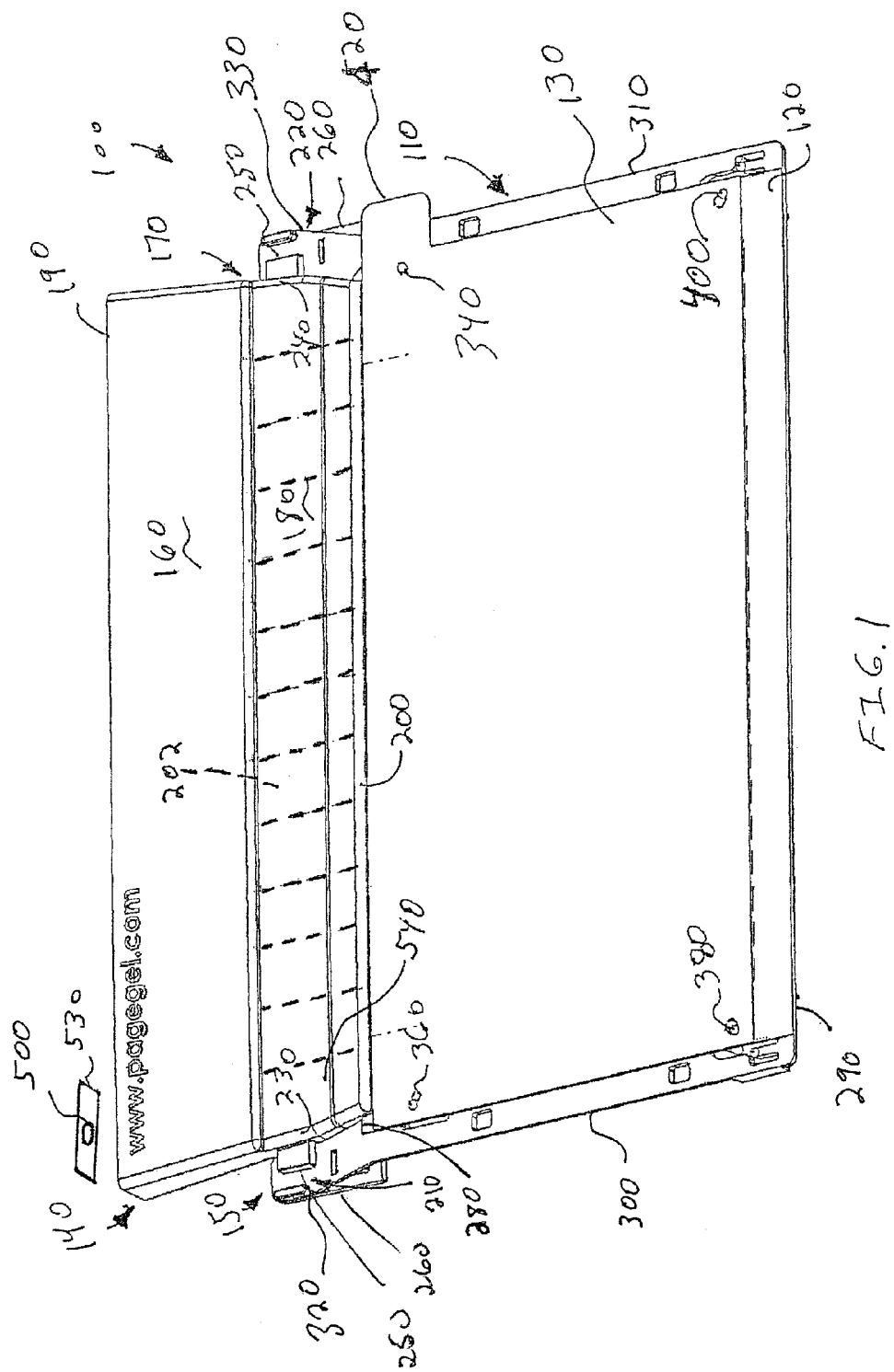
FIG. 1 is a perspective view of an embodiment of a thin-gel electrophoresis assembly with an embodiment of a protein marker pellet shown fixed to a substrate.

With reference to FIG. 1, an embodiment of a thin-film gel electrophoresis assembly 100 is shown. The electrophoresis assembly 100 may be used with an embodiment of a protein marker pellet of the present invention. The electrophoresis assembly 100 will first be described, followed by a description of an embodiment of a protein marker pellet of the present invention.

The thin-film gel electrophoresis assembly 100 includes a support frame 110 that carries a gel sandwiched between a first, inner thin-film member 120 and a second, outer thin-film member 130. A reservoir 140 is detachably mounted to a top 150 of the support frame 110. The thin-film gel electrophoresis assembly 100 shown is part of a vertical, sodium dodecyl sulphate polyacrylamide gel electrophoresis (SDS PAGE) gel electrophoresis system. The protein marker pellet described in detail below may be used with electrophoresis systems other than vertical, SDS PAGE gel electrophoresis systems.

The reservoir 140 includes an upper portion 160, and intermediate portion 170, and a lower portion 180 that gradually tapers in thickness from a wide, open top 190, where samples are introduced, to a narrow, open bottom 200, where the samples electrophoretically migrate from a first gel in the reservoir 140 to a second gel sandwiched between the thin-film members 120, 130. The upper portion 160 has a trough-like configuration. The lower portion 180 include a plurality of divided sample wells 202. Mounting mechanisms 210, 220 extend from opposite ends 230, 240 of the reservoir 140. Each mounting mechanism 210, 220 includes a first, small, front laterally protruding member 250 and a parallel second, large, rear laterally protruding member 260.

The support frame 110 is made of a flexible, resilient plastic material and has a substantially rectangular configuration. The support frame 110 includes an upper lateral support 280, a lower lateral support 290, a left vertical support 300, and a right vertical support 310. The vertical supports 300, 310 terminate at their tops 150 in ear-like protrusions 320, 330. The ear-like protrusions 320, 330 are slidably received between the front and rear protruding members 250, 260 of the mounting mechanisms 210, 220 for detachably mounting the reservoir 140 to the support frame 110.

A fixed support post 340 extends outwardly from the right vertical support 310 near an upper-right corner of the support frame 110. A support post 360 extends outwardly from the left vertical support 300 near an upper-left corner of the support frame 110. A support post 380 extends outwardly from the left vertical support 300 near a lower-left corner of the support frame 110. A support post 400 extends outwardly from the right vertical support 310 near a lower-right corner of the support frame 110.

The inner thin-film member 120 and outer thin-film member 130 are thin, rectangular pieces of plastic, transparent film such as cellophane film and include four holes that receive the four support posts for mounting the thin-film members 120, 130 to the support frame 110. The inner thin-film member 120 may include the second gel disposed on a front side. The outer thin-film member 130 may include a tabbed corner 420 to handle the outer thin-film member 130 and help orient it with respect to the support frame 110.

In operation, the electrophoresis assembly 100 is placed in an electrophoresis cell where the upper gel in the wells 202 of the reservoir 140 and the lower gel are in contact with buffer solutions which make electrical contact between the gels and the cathode or anode of an electrical power supply.

Figure 2:
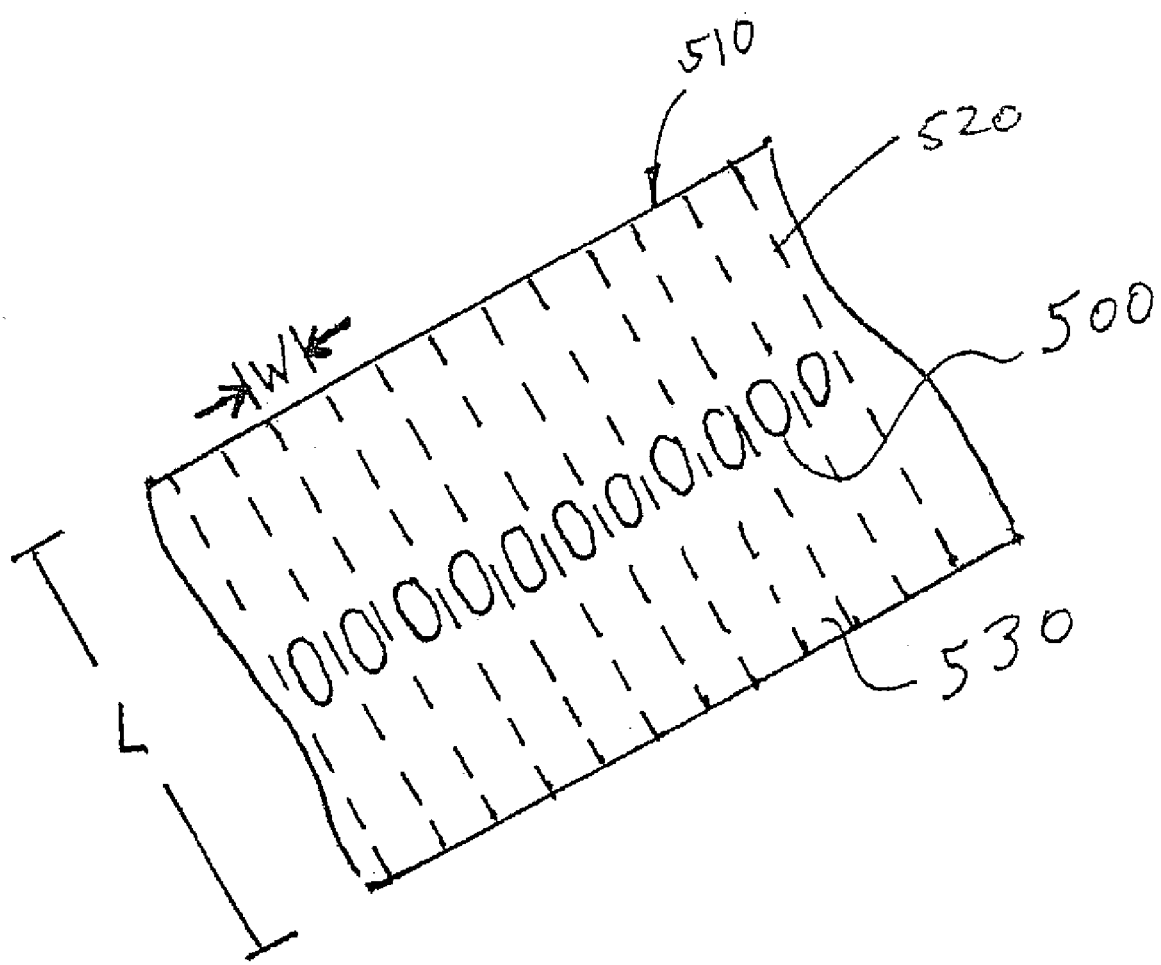
FIG. 2 is a top plan view of an embodiment of multiple protein marker pellets on substrates.

With reference to FIG. 2, an embodiment of a protein marker pellet 500 and method of making and using the same will now be described. The protein marker pellet 500 may have a obround shape and solid or semi-solid consistency. The protein marker pellet 500 includes a protein marker combined with a high-porosity, non-protein, gel-forming material. The protein marker(s) is one or more proteins of known molecular weight with ionic components to provide electrical conductance. The protein marker(s) preferably has a uniform charge density, should remain stacked or physically stable until entering the first gel, and has a tracking dye. The protein marker(s) are small enough to fit into the thickness of the electrophoresis gel. The pellet gel material has sufficient porosity to allow the protein marker(s) to migrate out of the pellet 500 under the influence of an electrical field at the same rate as the ions. The preferred gel-forming material is a thermal-setting polymer, such as high-melt agarose, at a concentration between 0.5 and 2%, preferably about 1% high-melt agarose. The pellet 500 has a density relative to that of the buffer solution for the first gel such that pellet 500 can remain around the upper surface of the first gel and at the bottom of a well 202. The pellet 500 may include protein markers of different sizes, SDS, buffer salts compatible with the first and second gels (e.g., may be the same as those present in the first and second gels), a density agent such as glycerol or di-methyl-formamide, and a tracking dye.

To make the protein marker pellet 500, a desired protein mixture of known molecular weight is combined with the gel-forming material and is dispensed either on a substrate or in a mold. To make the protein mixture, a solution containing the protein mixture and ions may be warmed to about 50° C. Similarly, a gel-forming material including 2.5% agarose may be warmed to about 50° C. The protein mixture may be mixed with the 2.5% agarose in a 3:2 ratio (i.e. three parts of the protein mixture may be mixed with 2 parts of 2.5% agarose). A tracking dye can also be added to the mixture. Small volumes (3 to 10 microliters) of the resulting protein marker pellet mixture is pipetted onto a suitable substrate 510 such as, but not limited to, a plastic film or a lacquer-coated paper and allowed to set into a gel. The paper substrate 510 may include lateral perforations 520 at intervals to form strips 530. The strips 530 may have a length L that is similar to the length of the wells 202 and a width W that is similar to the width of the wells 202. For example, each section may have a length L of 2 cm and a width W of 2.5 mm and each pellet 500 may have a width of 1 mm and a length of 2 mm.

Instead of a substrate 510, the protein marker pellet mixture may be dispensed into a mold to form obround, rod-shaped pellets that are a suitable length and diameter for the target electrophoresis gel.

With reference back to FIG. 1, the protein marker pellets 500 will now be described in use. In the embodiment shown, the thin-film gel electrophoresis assembly 100 includes thirteen wells. A protein marker well 540 may receive the protein marker pellet 500 and the other twelve wells 202 may receive the protein samples. A twelve-channel pipette may be used to fill the twelve wells with liquid protein samples. Before or after the liquid protein samples are loaded into the twelve wells 202, the protein marker pellet 500 may be loaded into the protein marker well 540. The protein marker 500 may be loaded with the substrate 530, with the protein marker pellet 500 faced down, as a single unit into the protein marker well 540.

The substrate 530 gives the protein marker 500 support for loading the pellet 500 into the well 540 and helps ensure central placement of the protein marker 500 on the upper surface of the top gel. The pellet placement process may be automated or done manually. The substrate 530 may carry more than one pellet 500 for loading into the well 540. Further, the reservoir 140 may include more than one protein marker well 540 that may receive one or more pellets 500. The pellets 500 may also be added to the protein marker well 540 without a substrate 530 attached.

In operation, the electrophoresis assembly 100 is placed into an electrophoresis cell (not shown) where the upper and the bottom gels are separately exposed to an electrolytic buffer. An electric potential is then applied to the buffer in contact with the upper and bottom gels, causing the protein samples and tracking dye to migrate toward the bottom of the lower gel. Simultaneously, the protein marker(s) migrates out of the pellet 500 under the influence of the electrical field at the same rate as the ions and into the upper and lower gels. After electrophoresis is completed, the locations of the bands of separated protein samples are then determined. By comparing the distance moved by particular bands of the protein samples in comparison to the protein marker(s), the mobility of protein samples can be determined. Once the mobility of the protein samples is determined, other characteristics such as the size of the proteins can be calculated.

Compared to prior-art protein markers, a free-flowing solution that must be pipetted into each well, the protein marker pellet(s) 500 confers several advantages. First, when used with multiple well gels, such as 13- or 26-well gels, that are filled from a multi-channel pipette, such as a 12-channel pipette, the protein marker pellet(s) 500 may be loaded without a pipette either before or after the multi-channel operation. Not having to pipette the protein marker into a well(s) saves effort, especially when large numbers of gels are loaded (e.g., loading eight gels simultaneously with 96-well automated loaders). Further, adding the protein marker pellet 500 can be easily automated.

Second, it is possible to load even a wide well, such as a 7.5 mm wide well, with a pellet 500, which during an electrophoresis separation maintains its narrow width. In such a wide well, a free-flowing marker solution would require more than three times the volume of the pellet 500 to give comparable sensitivity. Thus, the pellet 500 conserves the often-expensive marker solution saving costs.

Third, because the pellet is a solid/semi-solid, the pellet 500 is not put through the repeated freeze/thaw cycles that free-flowing marker solutions often are. Free-flowing marker solutions must be kept at low temperatures, which may cause the solution to freeze. To transfer the marker solution using a pipette, the marker solution must be thawed to a liquid state. Before a free-flowing marker solution is every pipetted into a well 202, it may have been through repeated freeze/thaw cycles. Repeated freeze/thaw cycles can cause degradation of proteins. By eliminating these repeated freeze/thaw cycles, the protein marker pellet 500 preserves stability of the proteins.

Finally, in gels using wide wells, such as 7.5 mm wide wells, it is possible to load multiple protein marker pellets 500 into the same well, providing distinct separations of markers when only one well is available. As examples, multiple different protein mark pellets 500 may be added to the same well if one wants to analyze more than one type of protein with a given gel or multiple protein mark pellets 500 of the same type may be added to the same well 202 to ensure that the protein marker is providing consistent results. If free-flowing marker solutions were employed, only one marker solution could be used in a well 202. If more than one marker solution was added to a well 202, the solutions would mix, giving confusing results. Thus, the protein marker pellets 500 enhance the information derived when the number of wells 202 available is limited.

It will be readily apparent to those skilled in the art that still further changes and modifications in the actual concepts described herein can readily be made without departing from the spirit and scope of the invention as defined by the following claims.

What is claimed is:

1. A protein marker pellet for use in a gel electrophoresis system, comprising:
   one or more protein markers including a protein of known molecular weight with ionic components to provide electrical conductance;
   a non-protein, gel-forming material having a porosity sufficient to allow the one or more protein markers to migrate out of the protein marker pellet under the influence of an electrical field at the same rate as the ionic components,
   wherein the protein marker pellet includes a density agent that is at least one of glycerol and di-methyl-formamide.

2. A protein marker pellet for use in a gel electrophoresis system, comprising:
   one or more protein markers including a protein of known molecular weight with ionic components to provide electrical conductance;
   a non-protein, gel-forming material having a porosity sufficient to allow the one or more protein markers to migrate out of the protein marker pellet under the influence of an electrical field at the same rate as the ionic components; and
   pellet is fixed to.

3. The protein marker pellet of claim 2, wherein the gel electrophoresis system includes a reservoir with multiple wells having a length and a width, and the substrate includes a length and a width substantially the same as the length and the width of the multiple wells.

4. A method of making a-protein marker pellets for use in a gel electrophoresis system, comprising:
   providing a protein marker solution including one or more protein markers having a protein of known molecular weight with ionic components to provide electrical conductance;
   providing a non-protein, gel-forming solution;
   warming the protein marker solution and the gel-forming solution;
   combining the protein marker solution and the gel-forming solution to form a protein marker gel solution;
   providing the protein marker gel solution into multiple small volumes of protein marker gel solution;
   allowing the multiple small volumes of protein marker gel solution to set so as to form multiple protein marker pellets having a porosity sufficient to allow the protein marker to migrate out of the protein marker pellets under the influence of an electrical field at the same rate as the ionic components.

5. The protein marker pellet of claim 4, wherein the gel electrophoresis system is a SDS PAGE gel electrophoresis system.

6. The method of claim 4, wherein the protein marker pellets are at least one of a solid and a semi-solid.

7. The method of claim 4, wherein the gel-forming solution is a thermal-setting polymer.

8. The method of claim 7, wherein the thermal-setting polymer is high-melt agarose.

9. The method of claim 8, wherein the high-melt agarose includes an agarose concentration between 0.5 and 2%.

10. The method of claim 9, wherein the agarose concentration is about 1%.

11. The method of claim 4, wherein the one or more protein markers include multiple protein markers with proteins of different sizes.

12. The method of claim 4, wherein the protein marker pellets includes SDS.

13. The method of claim 4, wherein the protein marker pellets includes buffer salts compatible with the gel electrophoresis system.

14. The method of claim 4, wherein the protein marker pellets include a density agent.

15. The method of claim 14, wherein the density agent is at least one of glycerol and di-methyl-formamide.

16. The method of claim 4, further including dropping the protein marker gel solution into multiple small volumes of protein marker gel solution onto a substrate.

17. The method of claim 16, wherein the substrate is paper.

18. The method of claim 17, wherein the paper is a lacquer-coated paper.

19. The method of claim 16, wherein the substrate is plastic film.

20. The method of claim 16, wherein the substrate includes perforations.

21. The method of claim 16, wherein the gel electrophoresis system includes a reservoir with multiple wells having a length and a width, and the substrate includes multiple strips of a length and a width substantially the same as the length and the width of the multiple wells.

22. The method of claim 4, wherein warming the protein marker solution includes warming the protein marker solution to about 50 degrees C.

23. The method of claim 4, wherein warming the gel-forming solution includes warming the gel-forming solution to about 50 degrees C.

24. The method of claim 4, wherein combining the protein marker solution and the gel-forming solution includes combining the protein marker solution with the gel-forming solution in substantially a 3:2 ratio.

25. The method of claim 4, wherein the small volumes of protein marker gel solution are 3 to 10 microliters.

26. A method of using a protein marker pellet with a gel electrophoresis system including multiple wells and an electrophoresis gel, comprising:
providing a protein marker pellet including one or more protein markers having a protein of known molecular weight with ionic components to provide electrical conductance, and a non-protein, gel-forming material having a porosity sufficient to allow the protein marker to migrate out of the protein marker pellet under the influence of an electrical field at the same rate as the ionic components;
depositing the protein marker pellet in one of the wells of the gel electrophoresis system;
causing the protein marker to migrate out of the protein marker pellet under the influence of an electrical field.

27. The method of claim 26, wherein the protein marker pellet is at least one of a solid and a semi-solid.

28. The method of claim 26, wherein the gel-forming material is a thermal-setting polymer.

29. The method of claim 28, wherein the thermal-setting polymer is high-melt agarose.

30. The method of claim 29, wherein the high-melt agarose includes an agarose concentration between 0.5 and 2%.

31. The method of claim 30, wherein the agarose concentration is about 1%.

32. The method of claim 26, wherein the one or more protein markers include multiple protein markers with proteins of different sizes.

33. The method of claim 26, wherein the protein marker pellet includes SDS.

34. The method of claim 26, wherein the protein marker pellet includes buffer salts compatible with the gel electrophoresis system.

35. The method of claim 26, wherein the protein marker pellet includes a density agent.

36. The method of claim 35, wherein the density agent is at least one of glycerol and di-methyl-formamide.

37. The method of claim 26, further including a substrate that the protein marker pellet is fixed to, and depositing the protein marker pellet includes depositing the protein marker pellet in one of the wells onto an electrophoresis gel with the protein mark pellet faced down.

38. The method of claim 37, wherein the gel electrophoresis system includes a reservoir with multiple wells having a length and a width, and the substrate includes a length and a width substantially the same as the length and the width of the multiple wells.

* * * * *